US011830625B2

(12) United States Patent
Sun et al.

(10) Patent No.: US 11,830,625 B2
(45) Date of Patent: Nov. 28, 2023

(54) GENERATION OF A DISEASE STATUS INDEX USING A PROBABILISTIC MODEL AND OBSERVATIONAL DATA

(71) Applicant: International Business Machines Corporation, Armonk, NY (US)

(72) Inventors: Zhaonan Sun, Elmsford, NY (US); Liuyi Yao, Amherst, NY (US); Zijun Yao, Ridgewood, NJ (US); Jianying Hu, Bronx, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 450 days.

(21) Appl. No.: 16/751,541

(22) Filed: Jan. 24, 2020

(65) Prior Publication Data
US 2021/0233662 A1    Jul. 29, 2021

(51) Int. Cl.
G16H 50/30 (2018.01)
G16H 10/60 (2018.01)
G06N 20/00 (2019.01)
G06F 17/18 (2006.01)
G06N 7/01 (2023.01)

(52) U.S. Cl.
CPC ............. *G16H 50/30* (2018.01); *G06F 17/18* (2013.01); *G06N 7/01* (2023.01); *G06N 20/00* (2019.01); *G16H 10/60* (2018.01)

(58) Field of Classification Search
None
See application file for complete search history.

(56) References Cited

U.S. PATENT DOCUMENTS

2004/0024534 A1    2/2004    Hsu
2007/0081701 A1    4/2007    Sirohey et al.
2009/0299769 A1    12/2009   Dam et al.
(Continued)

FOREIGN PATENT DOCUMENTS

WO    WO-2015023674 A1 *   2/2015   ........... G06F 3/0484

OTHER PUBLICATIONS

Trang Pham, DeepCare: A Deep Dynamic Memory Model for Predictive Medicine, Apr. 12, 2017, Cornell Univeristy, arXiv: 1602.00357 (Year: 2017).*
(Continued)

*Primary Examiner* — Shelby A Turner
*Assistant Examiner* — Matthew H Divelbiss
(74) *Attorney, Agent, or Firm* — Amin, Turocy & Watson, LLP

(57) ABSTRACT

Systems, computer-implemented methods, and computer program products to facilitate employing a probabilistic model to generate a continuous disease status index based on observational data are provided. According to an embodiment, a system can comprise a memory that stores computer executable components and a processor that executes the computer executable components stored in the memory. The computer executable components can comprise a model component that employs a probabilistic model to generate probability distributions of disease states of a disease of an entity based on observational data of the entity. The computer executable components can further comprise an index component that generates a disease status index of the disease based on the probability distributions of the disease states.

20 Claims, 11 Drawing Sheets

(56) References Cited

U.S. PATENT DOCUMENTS

| | | | |
|---|---|---|---|
| 2011/0112380 A1 | 5/2011 | Robinson | |
| 2013/0095459 A1* | 4/2013 | Tran | G09B 19/00 |
| | | | 434/247 |
| 2018/0014724 A1 | 1/2018 | Wroblewski | |
| 2018/0374582 A1 | 12/2018 | Holmes et al. | |
| 2019/0130070 A1* | 5/2019 | Cheng | G16H 50/50 |
| 2019/0374160 A1* | 12/2019 | Yin | A61B 5/14551 |

OTHER PUBLICATIONS

Lawton et al., "A longitudinal model for disease progression was developed and applied to multiple sclerosis," Journal of Clinical Epidemiology 68, 2015, pp. 1355-1365, 11 pages.

Jensen et al., "Mining electronic health records: towards better research applications and clinical care," Nature Reviews Genetics, Jun. 2012, vol. 13, pp. 395-405, 11 pages.

Long et al., "Validation of a Prognostic Index for Huntington's Disease," Movement Disorders, 2016, 8 pages.

Schobel et al., "Motor, cognitive, and functional declines contribute to a single progressive factor in early HD," American Academy of Neurology, 2017, 9 pages.

Fischer et al., "Prognostic Scoring Indices in Wilson Disease: A Case Series and Cautionary Tale," Journal of Pediatric Gastroenterology & Nutrition, Apr. 2011, vol. 52, Issue 4, pp. 466-469, 4 pages.

Sun et al., "A probabilistic disease progression modeling approach and its application to integrated Huntington's disease observational data," JAMIA Open, 2019, vol. 2, No. 1, pp. 123-130, 8 pages.

Mell et al., "The NIST Definition of Cloud Computing," Recommendations of the National Institute of Standards and Technology, NIST Special Publication 800-145, Sep. 2011, 7 pages.

* cited by examiner

GENERATION OF A DISEASE STATUS INDEX USING A PROBABILISTIC MODEL AND OBSERVATIONAL DATA

BACKGROUND

The subject disclosure relates to generating a disease status index, and more specifically, to generating a disease status index based on observational data.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, devices, computer-implemented methods, and/or computer program products that facilitate employing a probabilistic model to generate a continuous disease status index based on observational data are described.

According to an embodiment, a system can comprise a memory that stores computer executable components and a processor that executes the computer executable components stored in the memory. The computer executable components can comprise a model component that employs a probabilistic model to generate probability distributions of disease states of a disease of an entity based on observational data of the entity. The computer executable components can further comprise an index component that generates a disease status index of the disease based on the probability distributions of the disease states.

According to another embodiment, a computer-implemented method can comprise employing, by a system operatively coupled to a processor, a probabilistic model to generate probability distributions of disease states of a disease of an entity based on observational data of the entity. The computer-implemented method can further comprise generating, by the system, a disease status index of the disease based on the probability distributions of the disease states.

According to another embodiment, a computer program product facilitating a process to employ a probabilistic model to generate a continuous disease status index based on observational data is provided. The computer program product comprising a computer readable storage medium having program instructions embodied therewith, the program instructions executable by a processor to cause the processor to employ, by the processor, a probabilistic model to generate probability distributions of disease states of a disease of an entity based on observational data of the entity. The program instructions are further executable by the processor to cause the processor to generate, by the processor, a disease status index of the disease based on the probability distributions of the disease states.

DETAILED DESCRIPTION

Figure 1:
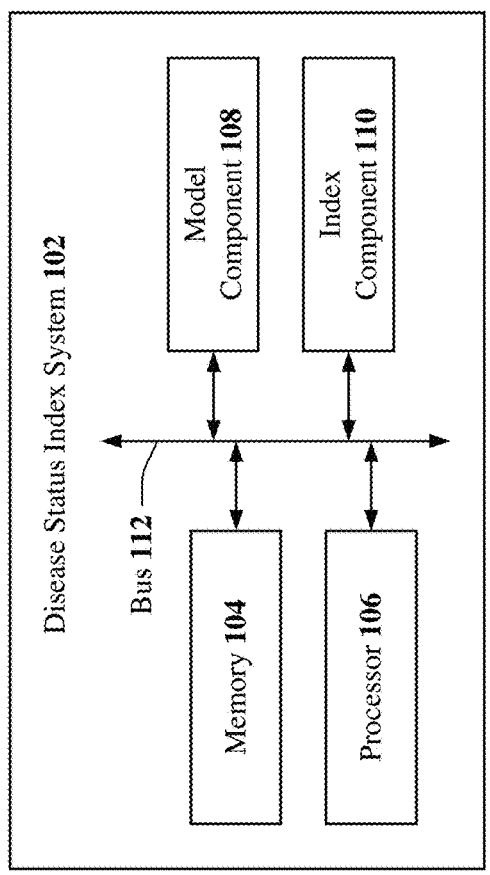
FIGS. 1 and 2 illustrate block diagrams of example, non-limiting systems that can facilitate employing a probabilistic model to generate a continuous disease status index based on observational data in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Chronic diseases often progress over extend period of time, causing great burden for patients, their families, as well as the society as a whole. It is crucial to have a simple and straight forward method for tracking disease progression. As referenced herein, disease and/or target disease can refer to a disease that an entity (e.g., a human) has and/or is at risk of contracting.

A disease progression index and/or a disease prognosis index (also referred to as a disease status index) is a single continuous measure that tracks the progression of a target disease. Such a disease status index can help physicians to quickly identify a patient's status, and therefore, can provide support for clinical decisions.

State-of-art methods for generating disease progression indices are based one or a small group of manually pre-selected measures, and use simple statistical models. Currently in clinical practice, there are two major ways for generating disease progression index: 1) use one single clinical assessment (e.g., glomerular filtration rate (GFR) for chronic kidney disease, hemoglobin A1c (HbA1c) for diabetes, etc.) as a progression index to track progression; and 2) pre-select (e.g., manually) a small group of clinical measures based on experts' input, and generate a composite score as progression index using simple models (e.g., a linear model). Such indices suffer from two issues: 1) a small group of pre-selected clinical measures could lead to biases in the disease progression indices; and 2) using simple statistical models could lead to large variation in the generated disease progression model.

Another problem with such existing methods for generating disease progression indices described above is that they often do not utilize observational data related to a patient and/or a target disease. Observational databases such as disease registry data and Electronic Health Records (EHR) contain high-dimensional heterogeneous longitudinal information about patients, and therefore, provide opportunities to build a disease progression index that can better track the progression of the disease.

Disease registry data follows patients who are at risk of or have a target disease. Multi-faceted information about the target disease is collected in a disease registry, which can be used to track disease progression. Dimension of all features collected in the disease registry can be large (e.g., medications, comorbidities, etc.). For example, a disease registry can contain: basic characteristics of participants (e.g., demographics, genotype, case status, control status, etc.); disease related information that can be reported by participants or collected by evaluators to provide additional participant characteristics; and/or clinical assessments from periodic visits that can be measured and recorded by clinicians or trained evaluators to monitor symptoms, disease progression, quality of life, cost burden of the disease, and/or another feature of the participant or the target disease.

Given the problems described above with existing technologies that generate disease progression indices using limited manually pre-selected measures and/or simple statistical models (e.g., linear models) to generate composite scores as progression indices, and technologies that fail to utilize observational data (e.g., EHR data, disease registry data, etc.), the present disclosure can be implemented to produce a solution to this problem in the form of systems, computer-implemented methods, and/or computer program products that can employ a probabilistic model (e.g., as opposed to a simple, linear model) to generate probability distributions of disease states of a disease of an entity based on observational data of the entity (e.g., high-dimensional heterogeneous longitudinal data of a patient collected in an EHR, a disease data registry, etc.); and/or generate a disease status index (e.g., a continuous disease status index) of the disease based on the probability distributions of the disease states. An advantage of such systems, computer-implemented methods, and/or computer program products is that they can improve the accuracy (e.g., completeness) of a disease status index and/or improve prognosis of a target disease by an expert entity (e.g., a human, a computing device, a software application, an expert agent, an artificial intelligence (AI) model, a machine learning (ML) model, etc.).

FIG. 1 illustrates a block diagram of an example, non-limiting system 100 that can facilitate employing a probabilistic model to generate a continuous disease status index based on observational data in accordance with one or more embodiments described herein. System 100 can comprise a disease status index system 102, which can be associated with a cloud computing environment. For example, disease status index system 102 can be associated with cloud computing environment 950 described below with reference to FIG. 9 and/or one or more functional abstraction layers described below with reference to FIG. 10 (e.g., hardware and software layer 1060, virtualization layer 1070, management layer 1080, and/or workloads layer 1090).

Disease status index system 102 and/or components thereof (e.g., model component 108, index component 110, extraction component 202, trainer component 204, etc.) can employ one or more computing resources of cloud computing environment 950 described below with reference to FIG. 9 and/or one or more functional abstraction layers (e.g., quantum software, etc.) described below with reference to FIG. 10 to execute one or more operations in accordance with one or more embodiments of the subject disclosure described herein. For example, cloud computing environment 950 and/or such one or more functional abstraction layers can comprise one or more classical computing devices (e.g., classical computer, classical processor, virtual machine, server, etc.), quantum hardware, and/or quantum software (e.g., quantum computing device, quantum computer, quantum processor, quantum circuit simulation software, superconducting circuit, etc.) that can be employed by disease status index system 102 and/or components thereof to execute one or more operations in accordance with one or more embodiments of the subject disclosure described herein. For instance, disease status index system 102 and/or components thereof can employ such one or more classical and/or quantum computing resources to execute one or more classical and/or quantum: mathematical function, calculation, and/or equation; computing and/or processing script; algorithm; model (e.g., artificial intelligence (AI) model, machine learning (ML) model, etc.); and/or another operation in accordance with one or more embodiments of the subject disclosure described herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Disease status index system 102 can comprise a memory 104, a processor 106, a model component 108, an index component 110, and/or a bus 112.

It should be appreciated that the embodiments of the subject disclosure depicted in various figures disclosed herein are for illustration only, and as such, the architecture of such embodiments are not limited to the systems, devices, and/or components depicted therein. For example, in some embodiments, system 100 and/or disease status index system 102 can further comprise various computer and/or computing-based elements described herein with reference to operating environment 800 and FIG. 8. In several embodiments, such computer and/or computing-based elements can be used in connection with implementing one or more of the systems, devices, components, and/or computer-implemented operations shown and described in connection with FIG. 1 or other figures disclosed herein.

Memory 104 can store one or more computer and/or machine readable, writable, and/or executable components and/or instructions that, when executed by processor 106 (e.g., a classical processor, a quantum processor, etc.), can facilitate performance of operations defined by the executable component(s) and/or instruction(s). For example, memory 104 can store computer and/or machine readable, writable, and/or executable components and/or instructions that, when executed by processor 106, can facilitate execution of the various functions described herein relating to disease status index system 102, model component 108, index component 110, and/or another component associated with disease status index system 102 (e.g., extraction component 202, trainer component 204, etc.), as described herein with or without reference to the various figures of the subject disclosure.

Memory 104 can comprise volatile memory (e.g., random access memory (RAM), static RAM (SRAM), dynamic RAM (DRAM), etc.) and/or non-volatile memory (e.g., read only memory (ROM), programmable ROM (PROM), electrically programmable ROM (EPROM), electrically erasable programmable ROM (EEPROM), etc.) that can employ one or more memory architectures. Further examples of memory 104 are described below with reference to system memory 816 and FIG. 8. Such examples of memory 104 can be employed to implement any embodiments of the subject disclosure.

Processor 106 can comprise one or more types of processors and/or electronic circuitry (e.g., a classical processor, a quantum processor, etc.) that can implement one or more computer and/or machine readable, writable, and/or executable components and/or instructions that can be stored on memory 104. For example, processor 106 can perform various operations that can be specified by such computer and/or machine readable, writable, and/or executable components and/or instructions including, but not limited to, logic, control, input/output (I/O), arithmetic, and/or the like. In some embodiments, processor 106 can comprise one or more central processing unit, multi-core processor, microprocessor, dual microprocessors, microcontroller, System on a Chip (SOC), array processor, vector processor, quantum processor, and/or another type of processor. Further examples of processor 106 are described below with reference to processing unit 814 and FIG. 8. Such examples of processor 106 can be employed to implement any embodiments of the subject disclosure.

Disease status index system 102, memory 104, processor 106, model component 108, index component 110, and/or another component of disease status index system 102 as described herein (e.g., extraction component 202, trainer component 204, etc.) can be communicatively, electrically, operatively, and/or optically coupled to one another via a bus 112 to perform functions of system 100, disease status index system 102, and/or any components coupled therewith. Bus 112 can comprise one or more memory bus, memory controller, peripheral bus, external bus, local bus, a quantum bus, and/or another type of bus that can employ various bus architectures. Further examples of bus 112 are described below with reference to system bus 818 and FIG. 8. Such examples of bus 112 can be employed to implement any embodiments of the subject disclosure.

Disease status index system 102 can comprise any type of component, machine, device, facility, apparatus, and/or instrument that comprises a processor and/or can be capable of effective and/or operative communication with a wired and/or wireless network. All such embodiments are envisioned. For example, disease status index system 102 can comprise a server device, a computing device, a general-purpose computer, a special-purpose computer, a quantum computing device (e.g., a quantum computer), a tablet computing device, a handheld device, a server class computing machine and/or database, a laptop computer, a notebook computer, a desktop computer, a cell phone, a smart phone, a consumer appliance and/or instrumentation, an industrial and/or commercial device, a digital assistant, a multimedia Internet enabled phone, a multimedia players, and/or another type of device.

Disease status index system 102 can be coupled (e.g., communicatively, electrically, operatively, optically, etc.) to one or more external systems, sources, and/or devices (e.g., classical and/or quantum computing devices, communication devices, etc.) via a data cable (e.g., High-Definition Multimedia Interface (HDMI), recommended standard (RS) 232, Ethernet cable, etc.). In some embodiments, disease status index system 102 can be coupled (e.g., communicatively, electrically, operatively, optically, etc.) to one or more external systems, sources, and/or devices (e.g., classical and/or quantum computing devices, communication devices, etc.) via a network.

In some embodiments, such a network can comprise wired and wireless networks, including, but not limited to, a cellular network, a wide area network (WAN) (e.g., the Internet) or a local area network (LAN). For example, disease status index system 102 can communicate with one or more external systems, sources, and/or devices, for instance, computing devices (and vice versa) using virtually any desired wired or wireless technology, including but not limited to: wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Zigbee and other 802.XX wireless technologies and/or legacy telecommunication technologies, BLUETOOTH®, Session Initiation Protocol (SIP), ZIGBEE®, RF4CE protocol, WirelessHART protocol, 6LoWPAN (IPv6 over Low power Wireless Area Networks), Z-Wave, an ANT, an ultra-wideband (UWB) standard protocol, and/or other proprietary and non-proprietary communication protocols. In such an example, disease status index system 102 can thus include hardware (e.g., a central processing unit (CPU), a transceiver, a decoder, quantum hardware, a quantum processor, etc.), software (e.g., a set of threads, a set of processes, software in execution, quantum pulse schedule, quantum circuit, quantum gates, etc.) or a combination of hardware and software that facilitates communicating information between disease status index system 102 and external systems, sources, and/or devices (e.g., computing devices, communication devices, etc.).

Disease status index system 102 can comprise one or more computer and/or machine readable, writable, and/or executable components and/or instructions that, when executed by processor 106 (e.g., a classical processor, a quantum processor, etc.), can facilitate performance of operations defined by such component(s) and/or instruction(s). Further, in numerous embodiments, any component associated with disease status index system 102, as described herein with or without reference to the various figures of the subject disclosure, can comprise one or more computer and/or machine readable, writable, and/or executable components and/or instructions that, when executed by processor 106, can facilitate performance of operations defined by such component(s) and/or instruction(s). For example, model component 108, index component 110, and/or any other components associated with disease status index system 102 as disclosed herein (e.g., communicatively, electronically, operatively, and/or optically coupled with and/or employed by disease status index system 102), can comprise such computer and/or machine readable, writable, and/or executable component(s) and/or instruction(s). Consequently, according to numerous embodiments, disease status index system 102 and/or any components associated therewith as disclosed herein, can employ processor 106 to execute such computer and/or machine readable, writable, and/or executable component(s) and/or instruction(s) to facilitate performance of one or more operations described herein with reference to disease status index system 102 and/or any such components associated therewith.

Disease status index system 102 can facilitate (e.g., via processor 106) performance of operations executed by and/or associated with model component 108 and/or index component 110, and/or another component associated with disease status index system 102 as disclosed herein (e.g., extraction component 202, trainer component 204, etc.). For example, as described in detail below, disease status index system 102 can facilitate via processor 106 (e.g., a classical processor, a quantum processor, etc.): employing a probabilistic model to generate probability distributions of disease states of a disease of an entity based on observational data of the entity; and/or generating a disease status index of the disease based on the probability distributions of the disease states.

In another example, as described in detail below, disease status index system 102 can further facilitate via processor 106 (e.g., a classical processor, a quantum processor, etc.): training the probabilistic model to determine at least one of a number of disease states corresponding to different diseases or one or more parameters used to generate probability distributions corresponding to the number of disease states of the different diseases based on observational training data of multiple entities collected at multiple observation times; extracting from an observational database at least one of the observational data of the entity or observational training data comprising observational data of multiple entities collected at multiple observation times; employing the probabilistic model to generate the probability distributions of the disease states at multiple observation times of the entity; and/or generating the disease status index of the disease at multiple observation times of the entity to track at least one of status of the disease or progression of the disease, thereby facilitating at least one of improved accuracy of the disease status index or improved prognosis of the disease by an expert entity.

In the examples described above, the observational data can include, but is not limited to, longitudinal observational data, high dimensional observational data, heterogeneous observational data, high dimensional longitudinal heterogeneous observational data, disease registry data, electronic health record data, and/or other observational data. Additionally, or alternatively, in the examples described above, the disease status index can comprise a continuous disease status index.

Model component 108 can employ a probabilistic model to generate probability distributions of disease states of a disease of an entity based on observational data of the entity. For example, model component 108 can employ a probabilistic model including, but not limited to, a hidden Markov model, a probabilistic recurrent neural network model (probabilistic RNN model), and/or another probabilistic model that can model temporal patterns of one or more entities (e.g., an entity such as, for instance, a human, a patient, a client, a user, a computing device, a software application, an agent, a machine learning (ML) model, an artificial intelligence (AI) model, etc.)). In some embodiments, model component 108 can employ model 500 and/or model 600 described below and illustrated in FIGS. 5 and 6, respectively to generate probability distributions of disease states of a disease of an entity based on observational data of the entity.

The probability distributions described above that can be generated by model component 108 can describe the probability over disease states of a target disease for each patient at each observation time stamp (e.g., at each time each patient is observed by, for example, a doctor, an evaluator, a clinician, etc.). For instance, each probability distribution that can be generated by model component 108 each time an entity is observed can describe the probability of the entity being in one or more disease states based on observational data collected from the entity at each observation time. Each of such one or more disease states can describe a typical disease status along the natural course of the disease.

Model component 108 can employ one or more of the probabilistic models defined above to generate probability distributions of disease states of a disease of an entity based on observational data of the entity including, but not limited to, longitudinal observational data, high-dimensional observational data, heterogeneous observational data, high-dimensional longitudinal heterogeneous observational data, disease registry data, electronic health record data, assigned diagnosis data, medication data, laboratory results data, comorbidity data, event data, patient profile data, patient demographic data, genotype data, case status data, control status data, periodic assessment data, clinical assessment data, disease symptom data, disease progression data, patient quality of life data, disease cost burden data, measurements data, and/or other data corresponding to the entity (e.g., a human patient). Observational databases such as, for instance, disease registries and/or electronic health records (EHR) contain high-dimensional heterogeneous longitudinal information about patients that can be used as input to model component 108 and/or index component 110 to generate a disease status index that can better track the progression of the disease.

Disease registry data follows patients who are at risk of or have a target disease. Multi-faceted information about the target disease is collected in a disease registry, which can be used to track disease progression. Dimension of all features collected in the disease registry can be large (e.g., medications, comorbidities, etc.). For example, a disease registry can contain: basic characteristics of participants (e.g., demographics, genotype, case status, control status, etc.); disease related information that can be reported by participants or collected by evaluators to provide additional participant characteristics; and/or clinical assessments from periodic visits that can be measured and recorded by clinicians or trained evaluators to monitor symptoms, disease progression, quality of life, cost burden of the disease, and/or another feature of the participant or the target disease. Such high-dimensional heterogeneous longitudinal information about patients described above can be used as input to model component 108 and/or index component 110 to generate a disease status index (e.g., disease status index 402 described below and illustrated in FIG. 4) that can better track the progression of the disease.

Model component 108 can employ a probabilistic model to generate probability distributions of disease states at multiple observation times of an entity. For example, every time an entity is observed (e.g., a human patient observed by a doctor, an evaluator, a clinician, etc.), model component 108 can employ one or more of the probabilistic models defined above to generate one or more probability distributions of one or more disease states of a target disease using observational data corresponding to the entity that was collected at such an observation time. Such one or more probability distributions of one or more disease states that can be generated by model component 108 each time an entity is observed can be used as input by index component 110 to generate a disease status index of the disease that can facilitate improved prognosis (e.g., prediction, tracking, etc.) of the disease as described below.

Index component 110 can generate a disease status index of a disease based on probability distributions of disease states of the disease. For instance, index component 110 can generate a disease status index of a disease based on the probability distributions of the disease states of the disease that can be generated by model component 108 as described above.

In an example, index component 110 can generate a continuous disease status index of the disease based on the probability distributions of the disease states that can be generated by model component 108 as described above. For instance, index component 110 can generate a continuous-time disease status index of the disease based on the probability distributions of the disease states that can be generated by model component 108 as described above. In some embodiments, index component 110 can generate a continuous-time disease status index such as, for instance, disease status index 402 described below and illustrated in FIG. 4.

In an example, to facilitate generation of such a disease status index (e.g., a continuous disease status index, a continuous-time disease status index, etc.), index component 110 can use equation (1) below to generate a disease status index of a disease having, for instance, 9 disease states (e.g., as depicted in equation (1) below). In equation (1) defined below, DPI denotes disease progression index (also referred to as disease status index) and $p_s$ denotes the probability of an entity being in a certain disease state S. It should be appreciated that although the number N of disease states S is depicted in equation (1) as 9, in other examples, equation (1) can be used by index component 110 to generate a disease status index of a disease having a different number N of disease states S (e.g., 6 disease states, 12 disease states, etc.). In some embodiments, index component 110 can employ equation (1) to generate a disease status index of a disease having a number N of disease states S and instead of using all of the disease states S, index component 110 can use certain disease states S such as, for instance, the disease states S with the highest probabilities (e.g., the top 2 or 3 disease states S with the highest probabilities).

$$DPI = \sum_{S=1}^{9} p_s * S \quad (1)$$

Index component 110 can generate a disease status index of a disease at multiple observation times of an entity to track at least one of status of the disease or progression of the disease, thereby facilitating at least one of improved accuracy of the disease status index or improved prognosis of the disease by an expert entity. For example, every time an entity is observed (e.g., a human patient observed by a doctor, an evaluator, a clinician, etc.), model component 108 can employ one or more of the probabilistic models defined above to generate one or more probability distributions of one or more disease states of a target disease using observational data corresponding to the entity that was collected at such an observation time. In this example, every time the entity is observed, index component 110 can use such one or more probability distributions of the one or more disease states as input to generate a disease status index of the disease (e.g., a continuous disease status index, a continuous-time disease status index, etc.), which can facilitate improved accuracy over existing disease progression indices and/or improved prognosis (e.g., prediction, tracking, etc.) of the disease.

Figure 2:
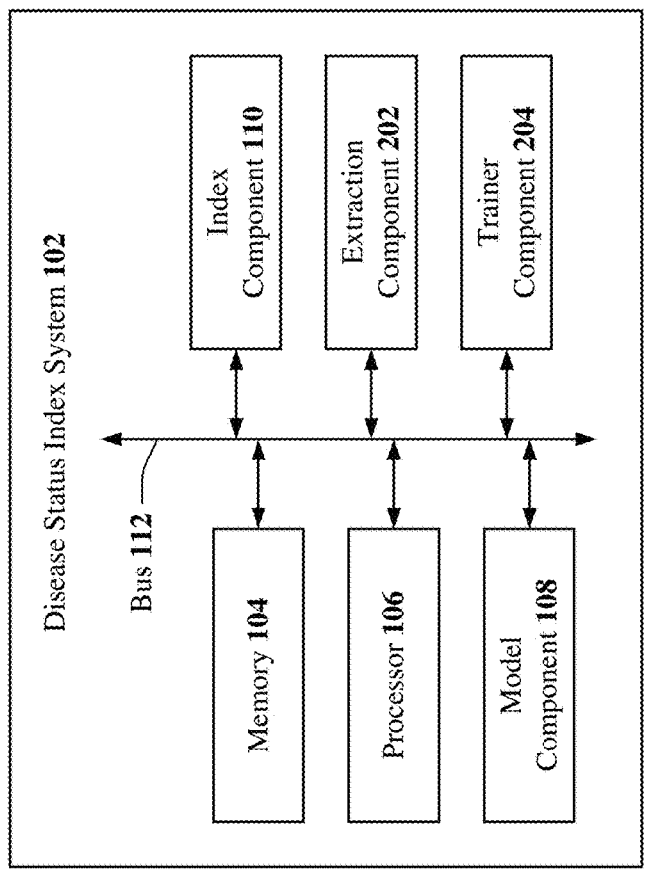

FIG. 2 illustrates a block diagram of an example, non-limiting system 200 that can facilitate employing a probabilistic model to generate a continuous disease status index based on observational data in accordance with one or more embodiments described herein. System 200 can comprise disease status index system 102. In some embodiments, disease status index system 102 can comprise an extraction component 202 and/or a trainer component 204. Repetitive description of like elements and/or processes employed in respective embodiments is omitted for sake of brevity.

Extraction component 202 can extract from an observational database at least one of observational data of an entity or observational training data comprising observational data of multiple entities collected at multiple observation times. For example, extraction component 202 can extract observational data and/or observational training data from an observational database including, but not limited to, an electronic health record (EHR), an electronic medical record (EMR), a disease registry, and/or another database comprising any of the observational data defined above that corresponds to one or more entities and is collected at one or more observation times.

Extraction component 202 can employ a model to extract such observational data and/or observational training data from one or more of such observational databases defined above. For example, to facilitate such extraction, extraction component 202 can employ a machine learning (ML) model based on artificial intelligence (AI), natural language processing (NLP), and/or named-entity recognition, including, but not limited to, a long short-term memory (LSTM) model, a bidirectional LSTM model with a conditional random field (CRF) layer (abbreviated as BiLSTM-CRF), a pretrained language model (e.g., transformer based) fine-tuning, a shallow or deep neural network model, a convolutional neural network (CNN) model, a support vector machine (SVM) model, a decision tree classifier, and/or any supervised or unsupervised machine learning model.

Extraction component 202 can employ one or more of such models defined above to extract observational data and/or observational training data corresponding to one or more entities that can be collected at one or more observational times, where such one or more observational databases can comprise structured and/or unstructured data. Extraction component 202 can employ one or more models defined above to extract observational data and/or observational training data corresponding to one or more entities that can be collected at one or more observation times, where such observational data and/or observational training data can include, but is not limited to, longitudinal observational data, high-dimensional observational data, heterogeneous observational data, high-dimensional longitudinal heterogeneous observational data, disease registry data, electronic health record data, assigned diagnosis data, medication data, laboratory results data, comorbidity data, event data, patient profile data, patient demographic data, genotype data, case status data, control status data, periodic assessment data, clinical assessment data, disease symptom data, disease progression data, patient quality of life data, disease cost burden data, measurements data, and/or other data corresponding to such one or more entities (e.g., a human patient).

In an example, every time an entity is observed (e.g., a human patient observed by a doctor, an evaluator, a clinician, etc.), extraction component 202 can employ one or more of such models defined above to extract observational data corresponding to the entity, where such extracted observational data can be used as input by model component 108 and/or index component 110 to generate one or more probability distributions of one or more disease states and/or to generate a disease status index, respectively, as described above. In another example, extraction component 202 can employ one or more of such models defined above to extract observational training data corresponding to multiple entities that has been collected at multiple observation times that can be used by trainer component 204 to train one or more of the models used by model component 108 as described below.

Trainer component 204 can train a probabilistic model to determine at least one of a number of disease states corresponding to different diseases or one or more parameters used to generate probability distributions corresponding to the number of disease states of the different diseases based on observational training data of multiple entities collected at multiple observation times. For example, trainer component 204 can train a probabilistic model to determine at least one of a number of disease states corresponding to different diseases or one or more parameters used by model component 108 to generate probability distributions corresponding to the number of disease states of the different diseases based on observational training data of multiple entities collected at multiple observation times that can be extracted from one or more observational databases by extraction component 202 as described above.

Trainer component 204 can comprise and/or employ one or more artificial intelligence (AI) models and/or one or more machine learning (ML) models to train one or more probabilistic models (e.g., a hidden Markov model, a probabilistic recurrent neural network model (probabilistic RNN model), etc.) to determine at least one of a number of disease states corresponding to different diseases or one or more parameters used by model component 108 to generate probability distributions corresponding to the number of disease states of the different diseases based on observational training data of multiple entities collected at multiple observation times. For example, trainer component 204 can comprise and/or employ one or more AI and/or ML models to train one or more probabilistic models (e.g., a hidden Markov model, a probabilistic RNN model, etc.) using one or more unsupervised learning methods.

Trainer component 204 can train a model (e.g., a hidden Markov model, a probabilistic RNN model, etc.) to determine the number of disease states and/or the one or more parameters described above based on classifications, correlations, inferences and/or expressions associated with principles of artificial intelligence. For instance, trainer component 204 can employ an automatic classification system and/or an automatic classification process to train a model (e.g., a hidden Markov model, a probabilistic RNN model, etc.) to determine the number of disease states and/or the one or more parameters described above. In one embodiment, trainer component 204 can employ a probabilistic and/or statistical-based analysis (e.g., factoring into the analysis utilities and costs) to train a model (e.g., a hidden Markov model, a probabilistic RNN model, etc.) to determine the number of disease states and/or the one or more parameters described above.

Trainer component 204 can employ any suitable machine learning based techniques, statistical-based techniques, and/or probabilistic-based techniques to train a model (e.g., a hidden Markov model, a probabilistic RNN model, etc.) to determine the number of disease states and/or the one or more parameters described above. For example, trainer component 204 can employ an expert system, fuzzy logic, support vector machine (SVM), Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, and/or another model. In some embodiments, trainer component 204 can perform a set of machine learning computations associated with training a model (e.g., a hidden Markov model, a probabilistic RNN model, etc.) to determine the number of disease states and/or the one or more parameters described above. For example, trainer component 204 can perform a set of clustering machine learning computations, a set of logistic regression machine learning computations, a set of decision tree machine learning computations, a set of random forest machine learning computations, a set of regression tree machine learning computations, a set of least square machine learning computations, a set of instance-based machine learning computations, a set of regression machine learning computations, a set of support vector regression machine learning computations, a set of k-means machine learning computations, a set of spectral clustering machine learning computations, a set of rule learning machine learning computations, a set of Bayesian machine learning computations, a set of deep Boltzmann machine computations, a set of deep belief network computations, and/or a set of different machine learning computations to train a model (e.g., a hidden Markov model, a probabilistic RNN model, etc.) to determine the number of disease states and/or the one or more parameters described above.

Figure 3:
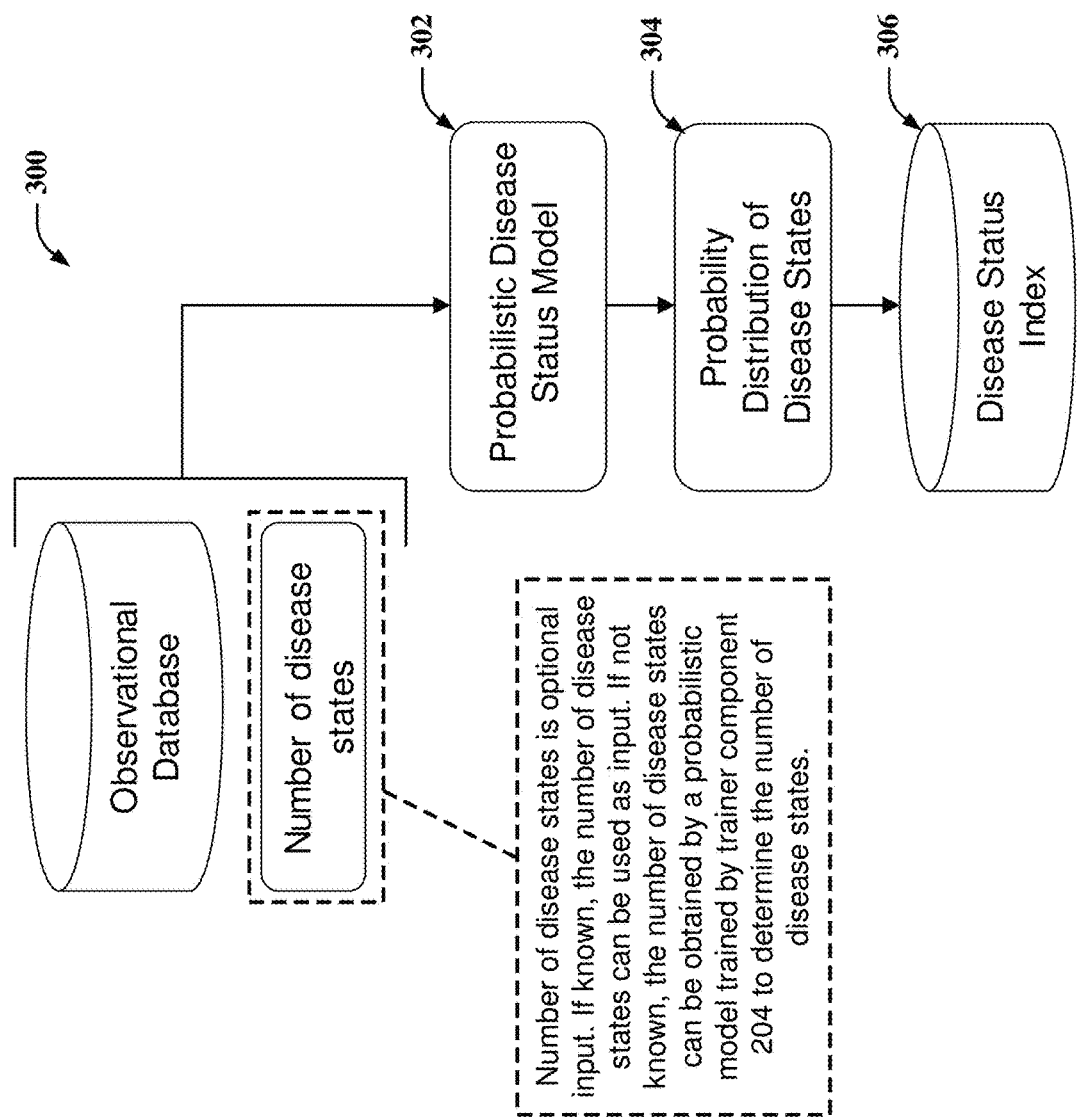
FIG. 3 illustrates a flow diagram of an example, non-limiting computer-implemented method that can facilitate employing a probabilistic model to generate a continuous disease status index based on observational data in accordance with one or more embodiments described herein.

FIG. 3 illustrates a flow diagram of an example, non-limiting computer-implemented method 300 that can facilitate employing a probabilistic model to generate a continuous disease status index based on observational data in accordance with one or more embodiments described herein. Repetitive description of like elements and/or processes employed in respective embodiments is omitted for sake of brevity.

At 302, computer-implemented method 300 can comprise inputting observational data corresponding to an entity and/or a number of disease states of a disease into a probabilistic disease status model (e.g., a hidden Markov model, a probabilistic RNN model, etc.). For example, as described above with reference to FIG. 2, extraction component 202 can extract such observational data from an observational database. In embodiments where the number of disease states is known, extraction component 202 can also extract such information from an observational database. In embodiments where the number of disease states is not known, as described above with reference to FIG. 2, trainer component 204 can train a probabilistic model to determine the number of disease states corresponding to different diseases. In these examples, such observational data and/or number of disease states can be used as input at 302 by model component 108.

At 304, computer-implemented method 300 can comprise generating one or more probability distributions of one or more disease states. For example, as described above with reference to FIG. 1, every time an entity is observed (e.g., a human patient observed by, for instance, a doctor, an evaluator, a clinician, etc.), model component 108 can employ a probabilistic model (e.g., a hidden Markov model, a probabilistic RNN model, etc.) to generate probability distributions of disease states of a disease based on observational data of the entity.

At 306, computer-implemented method 300 can comprise generating a disease status index based on the one or more probability distributions generated at 304 (e.g., by model component 108). For example, as described above with reference to FIG. 1, every time an entity is observed (e.g., a human patient observed by, for instance, a doctor, an evaluator, a clinician, etc.), model component 108 can employ a probabilistic model (e.g., a hidden Markov model, a probabilistic RNN model, etc.) to generate probability distributions of disease states of a disease based on observational data of the entity and index component 110 can employ equation (1) defined above to generate a disease status index (e.g., a continuous disease status index, a continuous-time disease status index, etc.) based on such probability distributions. For instance, at 306, index component 110 can generate a continuous-time disease status index that can serve as a single continuous measure for tracking the status of a patient over time.

Figure 4:
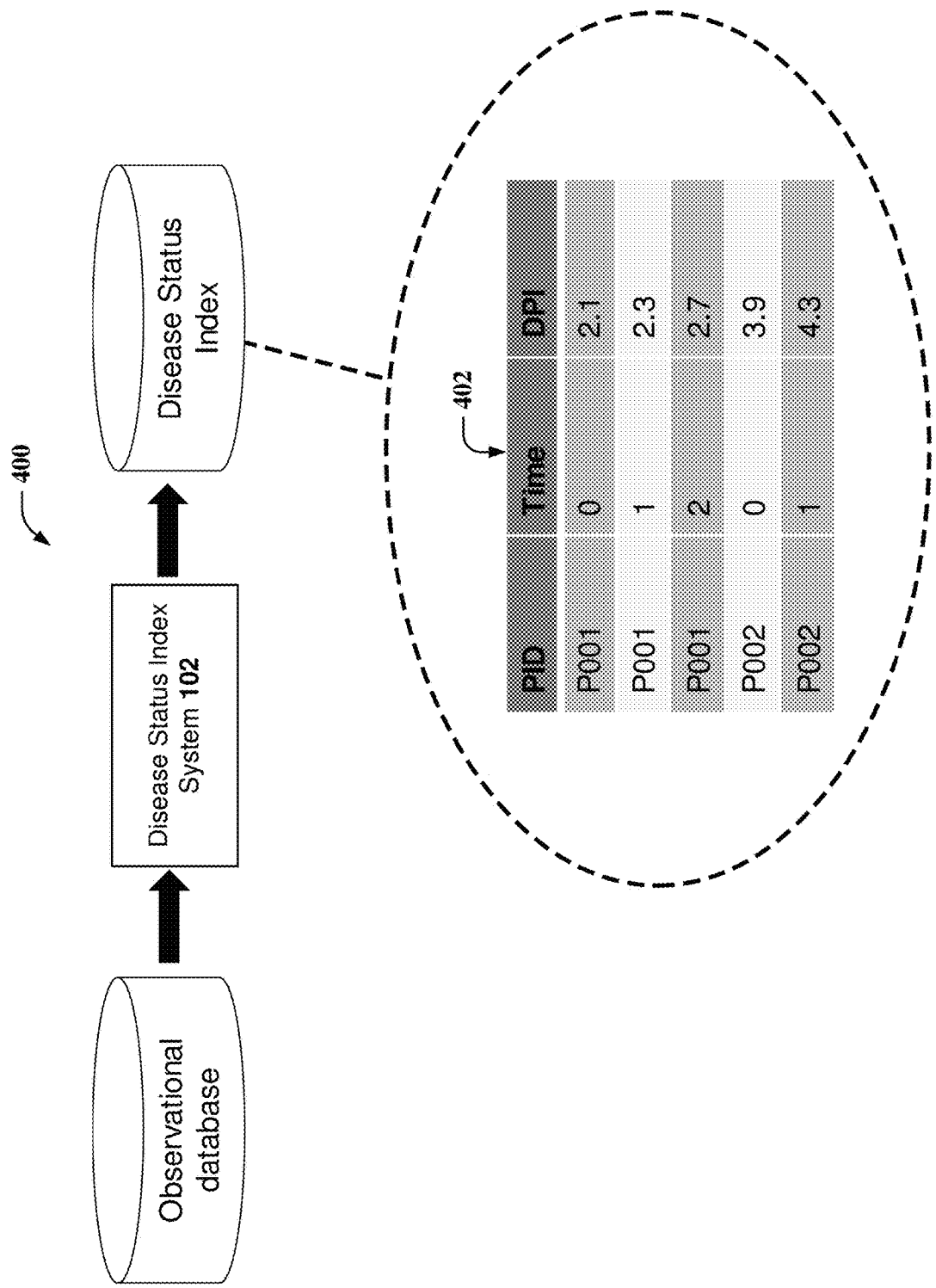
FIG. 4 illustrates a diagram of an example, non-limiting system that can facilitate employing a probabilistic model to generate a continuous disease status index based on observational data in accordance with one or more embodiments described herein.

FIG. 4 illustrates a diagram of an example, non-limiting system 400 that can facilitate employing a probabilistic model to generate a continuous disease status index based on observational data in accordance with one or more embodiments described herein. Repetitive description of like elements and/or processes employed in respective embodiments is omitted for sake of brevity.

As illustrated in FIG. 4 and described above with reference to FIGS. 1 and 2, every time an entity is observed (e.g., a human patient observed by, for instance, a doctor, an evaluator, a clinician, etc.), disease status index system 102 can extract (e.g., via extraction component 202) observational data corresponding to the entity from an observational database (e.g., an EHR, a disease registry, etc.) and generate (e.g., via model component 108 and index component 110) a disease status index. For example, disease status index system 102 (e.g., via model component 108, index component 110, etc.) can generate disease status index 402 depicted in FIG. 4 which can comprise a continuous disease status index (e.g., a continuous-time disease status index). Disease status index 402 can comprise a structured database that can be used by an expert entity (e.g., a human, a computing device, a software application, an expert agent, an artificial intelligence (AI) model, a machine learning (ML) model, etc.) to predict and/or track the progression of a disease through various disease states.

As illustrated in FIG. 4, disease status index 402 can comprise a patient identification column (denoted as PID in FIG. 4), a time column, and/or a disease progression index value column (denoted as DPI in FIG. 4). The patient identification (PID) column can comprise identification of one or more patients (denoted as P001 and P002 in FIG. 4) that can be tracked using disease status index system 102. The time column can denote each observation instance (denoted as 0, 1, and 2 in FIG. 4) when a patient is observed (e.g., a human patient observed by, for instance, a doctor, an evaluator, a clinician, etc.). The disease progression index (DPI) column (also referred to as disease status index column) can comprise the disease status index values that can be generated by disease status index system 102 (e.g., via model component 108, index component 110, etc.) each time a patient (e.g., P001, P002, etc.) is observed (e.g., at time 0, 1, 2, etc.).

The disease progression index values of disease status index 402 depicted in FIG. 4 can correspond to various degrees of progression through one or more disease states of a certain disease. For example, the disease progression index values of 2.1, 2.3, and 2.7 depicted in FIG. 4 for patient P001 can correspond to various degrees of progression through a disease state denoted as disease state 2 of a certain disease. In another example, the disease progression index values of 3.9 and 4.3 depicted in FIG. 4 for patient P002 can correspond to various degrees of progression through disease states denoted as disease state 3 and disease state 4, respectively, of a certain disease. It should be appreciated that such disease status index values are non-integer (e.g., fraction) values that can facilitate improved accuracy of disease status index 402 over existing disease progression indices that use integer values (e.g., composite scores) to represent the disease states. By providing such granularity of the various degrees of progression through a disease state(s) (e.g., DPI values of 2.1, 2.3, 2.7, 3.9, 4.3, etc.) disease status index system 102 (e.g., via model component 108, index component 110, etc.) can further facilitate improved prognosis (e.g., prediction, tracking, etc.) of the disease by an expert entity (e.g., a human, a computing device, a software application, an expert agent, an artificial intelligence (AI) model, a machine learning (ML) model, etc.) over existing disease progression indices that use integer values (e.g., composite scores) to represent the disease states.

Figure 5:
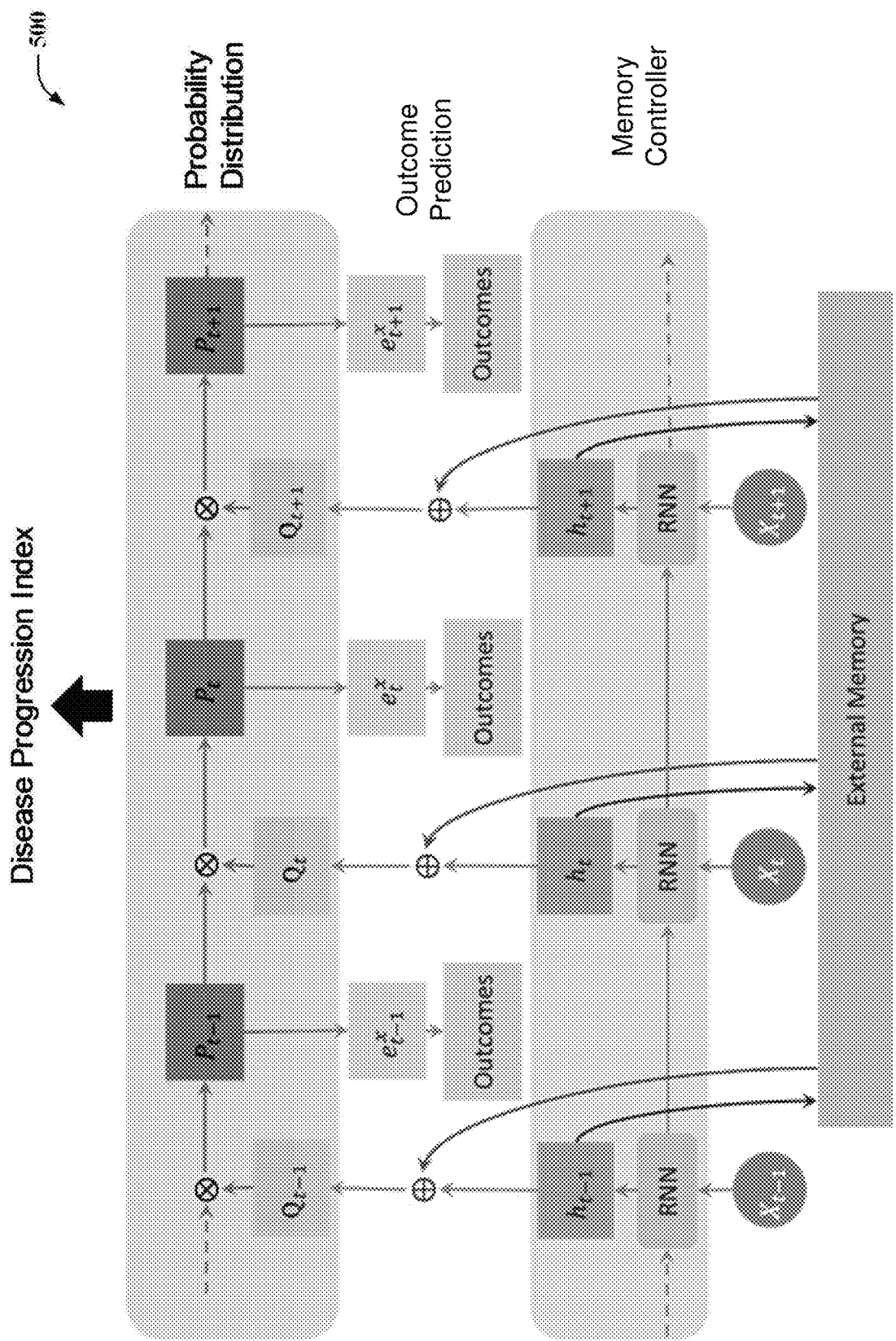
FIGS. 5 and 6 illustrate diagrams of example, non-limiting models that can facilitate employing a probabilistic model to generate a continuous disease status index based on observational data in accordance with one or more embodiments described herein.

FIG. 5 illustrates a diagram of an example, non-limiting model 500 that can facilitate employing a probabilistic model to generate a continuous disease status index based on observational data in accordance with one or more embodiments described herein. Repetitive description of like elements and/or processes employed in respective embodiments is omitted for sake of brevity.

Model 500 can comprise a probabilistic recurrent neural network model that can be employed by disease status index system 102 (e.g., model component 108, index component 110, etc.) to perform one or more of the operations that can be executed by disease status index system 102 and/or one or more components thereof in accordance with one or more embodiments of the subject disclosure described herein. As illustrated in FIG. 5, model 500 can comprise three components: a memory with controller layer (denoted as Memory Controller in FIG. 5), a state probability distribution layer (denoted as Probability Distribution in FIG. 5), and/or an outcome prediction layer (denoted as Outcome Prediction in FIG. 5).

The memory with controller layer can: consume observational data $X_t$, extract representation information $h_t$, and/or output the combined representation of current and past observations. The memory with controller layer can be implemented with a recurrent neural network (RNN) based controller which can store and retrieve disease progression information with an external memory matrix (denoted as External Memory in FIG. 5). The state probability distribution layer can: accept the output from the memory with controller layer, update the transition matrix $Q_t$, and generate the state probability distribution $P_t$. The outcome prediction layer can process the state probability distribution $P_t$ as representation $e_t^x$ and use it for predicting outcomes. The outcomes can be next time observation, current observation reconstruction, and time gap from the current to the next observation time.

Figure 6:
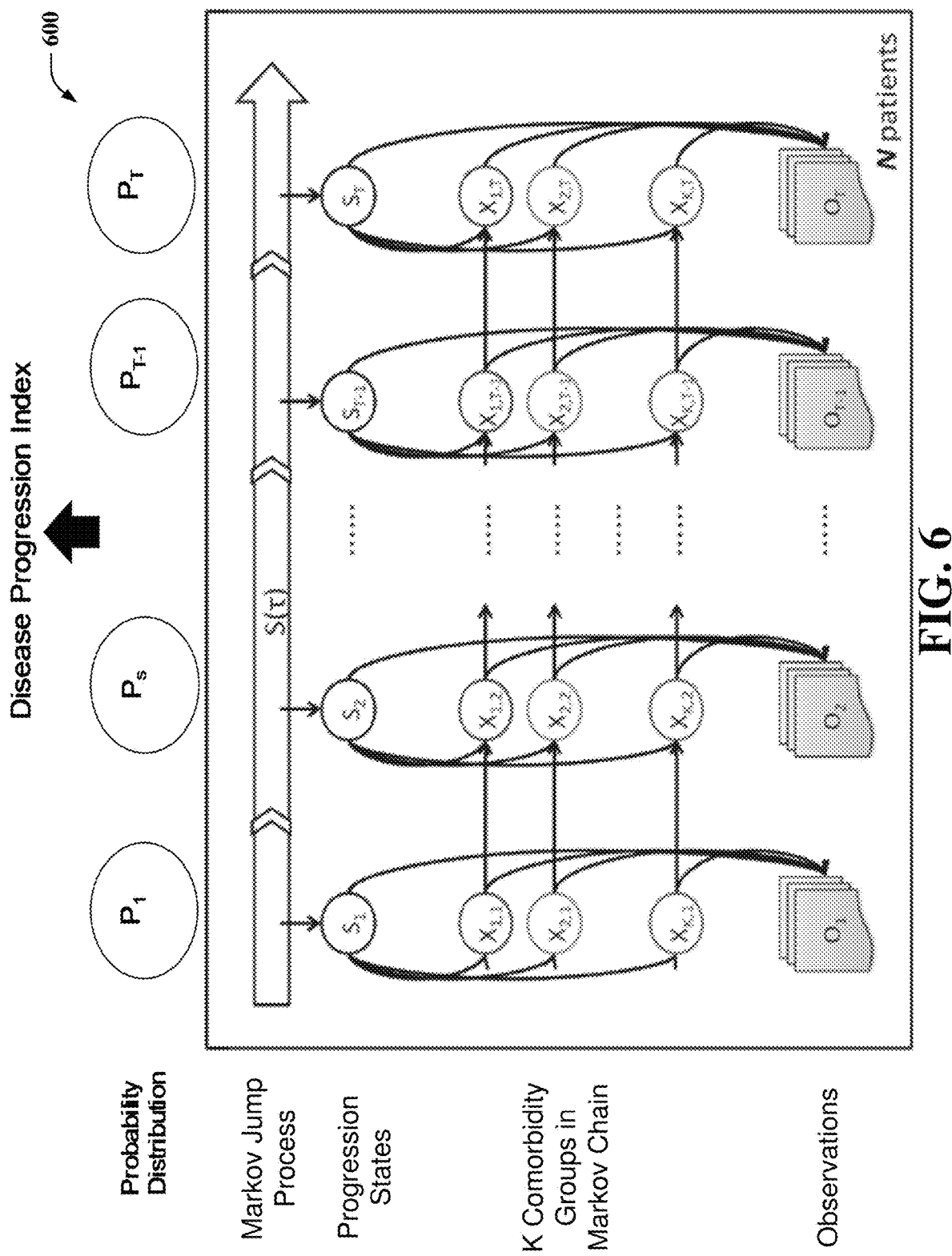

FIG. 6 illustrates a diagram of an example, non-limiting model 600 that can facilitate employing a probabilistic model to generate a continuous disease status index based on observational data in accordance with one or more embodiments described herein. Repetitive description of like elements and/or processes employed in respective embodiments is omitted for sake of brevity.

Model 600 can comprise a hidden Markov model that can be employed by disease status index system 102 (e.g., model component 108, index component 110, etc.) to perform one or more of the operations that can be executed by disease status index system 102 and/or one or more components thereof in accordance with one or more embodiments of the subject disclosure described herein. As illustrated in FIG. 6, model 600 can comprise three components: an observation layer (denoted as Observations in FIG. 6), a comorbidity layer (denoted as K Comorbidity Groups in Markov Chain in FIG. 6), and a Markov jump process layer (denoted as Markov Jump Process in FIG. 6).

The observation layer can consume the observational data $O_t$ and groups observations into comorbidities $X_{k,t}$. The comorbidity layer can output the onset pattern of a set of comorbidities which can be implemented using a set of Markov chains. The Markov jump process layer can: accept the output of comorbidity layer, model the progression of disease by capturing the transitions of state $S_t$ with hidden Markov model, and/or generate the state probability distribution $P_t$.

Disease status index system 102 can be associated with various technologies. For example, disease status index system 102 can be associated with disease progression index technologies, disease prognosis technologies, medical and/or healthcare records technologies, electronic health records technologies, electronic medical records technologies, machine learning technologies, artificial intelligence technologies, cloud computing technologies, and/or other technologies.

Disease status index system 102 can provide technical improvements to systems, devices, components, operational steps, and/or processing steps associated with the various technologies identified above. For example, disease status index system 102 can employ a probabilistic model to generate probability distributions of disease states of a disease of an entity based on observational data of the entity; and/or generate a disease status index of the disease based on the probability distributions of the disease states. Employing a probabilistic model to generate such probability distributions using observational data (e.g., high-dimensional longitudinal heterogeneous observational data) collected from the entity (e.g., a human patient) enables improved accuracy and/or granularity of the entity's progression through the various degrees of each disease state of a disease. By improving the accuracy and/or granularity of the entity's progression through the various degrees of each disease state of a disease, disease status index system 102 can thereby facilitate improved diagnosis, tracking, prognosis (e.g., prediction, etc.), and/or treatment recommendations by an expert entity (e.g., a human, a computing device, a software application, an expert agent, an artificial intelligence (AI) model, a machine learning (ML) model, etc.) over existing disease progression indices that use integer values (e.g., composite scores) to represent the disease states.

In an example, disease status index system 102 can improve disease tracking which in turn can improve prognosis and/or treatment by providing a single continuous disease status index that captures all observed aspects of signs and symptoms of the disease as it progresses. Disease status index system 102 overcomes the disadvantage of existing disease progression tracking technologies that rely on a single, or a small group of manually selected measures.

In another example, an expert agent (e.g., a computing device implementing an artificial intelligence and/or machine learning model) can be controlled and/or engineered to output a diagnosis, prognosis, and/or treatment recommendation based on a disease status index generated by the disease status index system 102. For instance, a disease status index generated by disease status index system 102 can be used to generate patient cohorts specific to a particular stage of the disease, and then diagnosis models, prognosis models, and/or treatment evaluation models can be trained on such cohorts (e.g., via trainer component 204). The expert agent defined above can then utilize the results of such models to provide diagnosis, prognosis, and/or treatment recommendations based on the disease status index generated by disease status index system 102.

In another example, a medicine dispenser can be controlled and/or engineered to output a specific quantity and/or type of medication based on a disease status index generated by disease status index system 102. For instance, as described above, a disease status index generated by disease status index system 102 can be used to generate patient cohorts specific to a particular stage of the disease, and then diagnosis models, prognosis models, and/or treatment evaluation models can be trained on such cohorts (e.g., via trainer component 204). The medicine dispenser can then utilize the results of such models to output a specific quantity and/or type of medication based on the disease status index generated by disease status index system 102.

Disease status index system 102 can provide technical improvements to a processing unit (e.g., processor 106) associated with a classical computing device and/or a quantum computing device (e.g., a quantum processor, quantum hardware, superconducting circuit, etc.) associated with disease status index system 102. For example, by improving the prognosis (e.g., prediction, tracking, etc.) of a disease by an expert entity such as, for instance, an expert agent (e.g., a computing device, a software application, an AI model, a ML model, etc.), disease status index system 102 can thereby facilitate more accurate and/or effective treatment recommendations by the expert agent. More accurate and/or effective treatment recommendations by such an expert agent that can utilize a processing unit (e.g., processor 106) to perform such prognosis and/or treatment recommendations can thereby facilitate reduced processing cycles by such a processing unit (e.g., processor 106) to generate such treatment recommendations, which can improve the efficiency of and/or reduce computational costs of the processing unit.

Based on such improved prognosis of one or more diseases, a practical application of disease status index system 102 is that it can be implemented by an expert entity such as, for instance, the expert agent defined above to better understand the lifecycle of a certain disease and/or the various factors that contribute to the progression or recession of the disease, and/or to recommend more effective treatments of the disease.

It should be appreciated that disease status index system 102 provides a new approach driven by relatively new expert agent technologies such as, for instance, automated expert agents that recommend treatment options to entities (e.g., human patients) that have or are at risk of contracting a certain disease. For example, disease status index system 102 provides a new approach to recommend accurate and/or effective treatment options for a disease based on observational data (e.g., EHR data, disease registry data, etc.) that is driven by existing technologies that generate disease progression indices using limited manually pre-selected measures and/or simple statistical models (e.g., linear models) that fail to utilize such observational data.

Disease status index system 102 can employ hardware or software to solve problems that are highly technical in nature, that are not abstract and that cannot be performed as a set of mental acts by a human. In some embodiments, one or more of the processes described herein can be performed by one or more specialized computers (e.g., a specialized processing unit, a specialized classical computer, a specialized quantum computer, etc.) to execute defined tasks related to the various technologies identified above. Disease status index system 102 and/or components thereof, can be employed to solve new problems that arise through advancements in technologies mentioned above, employment of quantum computing systems, cloud computing systems, computer architecture, and/or another technology.

It is to be appreciated that disease status index system 102 can utilize various combinations of electrical components, mechanical components, and circuitry that cannot be replicated in the mind of a human or performed by a human, as the various operations that can be executed by disease status index system 102 and/or components thereof as described herein are operations that are greater than the capability of a human mind. For instance, the amount of data processed, the speed of processing such data, or the types of data processed by disease status index system 102 over a certain period of time can be greater, faster, or different than the amount, speed, or data type that can be processed by a human mind over the same period of time.

According to several embodiments, disease status index system 102 can also be fully operational towards performing one or more other functions (e.g., fully powered on, fully executed, etc.) while also performing the various operations described herein. It should be appreciated that such simultaneous multi-operational execution is beyond the capability of a human mind. It should also be appreciated that disease status index system 102 can include information that is impossible to obtain manually by an entity, such as a human user. For example, the type, amount, and/or variety of information included in disease status index system 102, model component 108, index component 110, extraction component 202, and/or trainer component 204 can be more complex than information obtained manually by a human user.

Figure 7A:
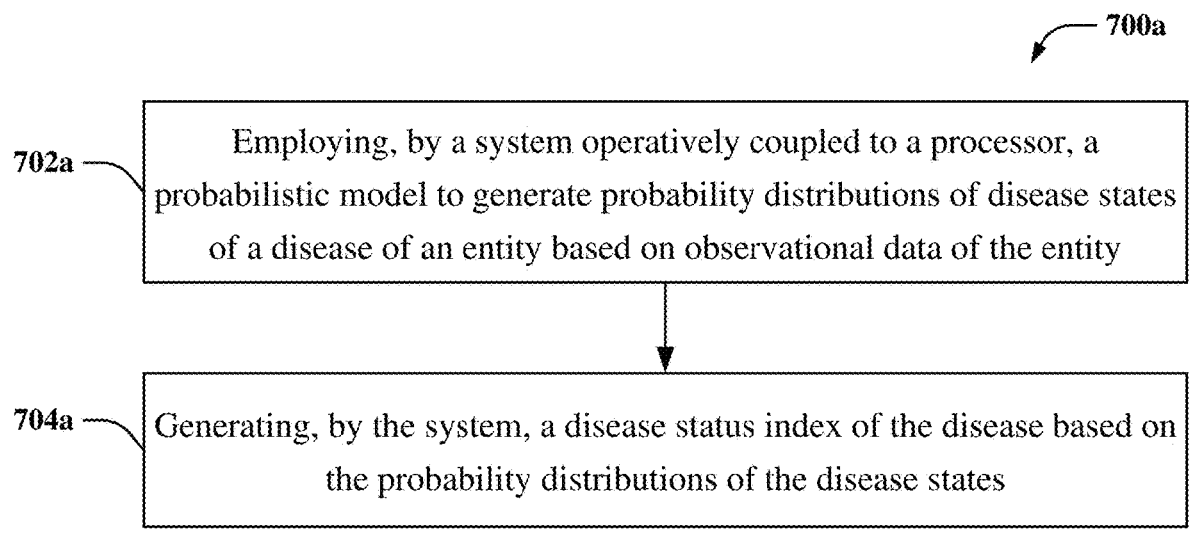
FIGS. 7A and 7B illustrate flow diagrams of example, non-limiting computer-implemented methods that can facilitate employing a probabilistic model to generate a continuous disease status index based on observational data in accordance with one or more embodiments described herein.

FIG. 7A illustrates a flow diagram of an example, non-limiting computer-implemented method 700a that can facilitate employing a probabilistic model to generate a continuous disease status index based on observational data in accordance with one or more embodiments described herein. Repetitive description of like elements and/or processes employed in respective embodiments is omitted for sake of brevity.

At 702a, computer-implemented method 700a can comprise employing, by a system (e.g., via disease status index system 102 and/or model component 108) operatively coupled to a processor (e.g., processor 106, a quantum processor, etc.), a probabilistic model (e.g., a hidden Markov model, a probabilistic RNN model, etc.) to generate probability distributions of disease states of a disease of an entity (e.g., a human patient) based on observational data (e.g., high-dimensional longitudinal heterogeneous observational data) of the entity.

At 704a, computer-implemented method 700a can comprise generating, by the system (e.g., via disease status index system 102 and/or index component 110), a disease status index (e.g., disease status index 402, a continuous disease status index, a continuous-time disease status index, etc.) of the disease based on the probability distributions of the disease states.

Figure 7B:
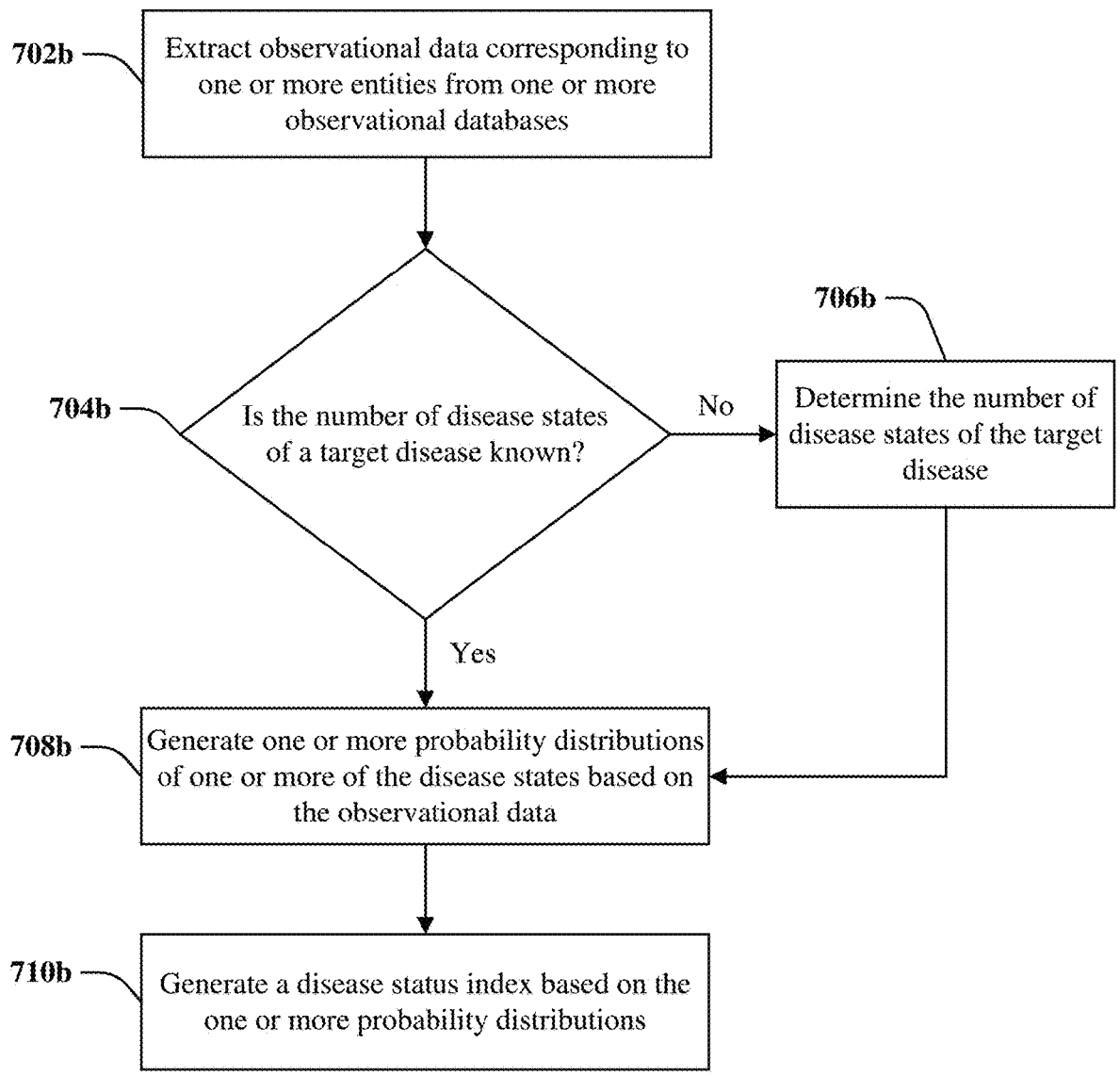

FIG. 7B illustrates a flow diagram of an example, non-limiting computer-implemented method 700b that can facilitate employing a probabilistic model to generate a continuous disease status index based on observational data in accordance with one or more embodiments described herein. Repetitive description of like elements and/or processes employed in respective embodiments is omitted for sake of brevity.

At 702b, computer-implemented method 700b can comprise extracting (e.g., via disease status index system 102 and/or extraction component 202) observational data (e.g., high-dimensional longitudinal heterogeneous observational data) corresponding to one or more entities (e.g., human patient(s), etc.) from one or more observational databases (e.g., EHR data, disease registry data, etc.). For example, as described above with reference to FIG. 2, extraction component 202 can extract from an observational database at least one of observational data of an entity or observational training data comprising observational data of multiple entities collected at multiple observation times.

At 704b, computer-implemented method 700b can comprise determining (e.g., via disease status index system 102, model component 108, extraction component 202, trainer component 204, etc.) whether the number of disease states of a target disease are known. If it is determined at 704b that the number of disease states are not known, at 706b, computer-implemented method 700b can comprise determining (e.g., model component 108) the number of disease states of the target disease. For example, as described above with reference to FIGS. 1 and 2, trainer component 204 can train a probabilistic model (e.g., a hidden Markov model, a probabilistic RNN model, etc.) that can be employed by model component 108 to determine the number of disease states of a disease using observational training data corresponding to multiple entities observed at multiple observation times, where such observational training data can be extracted from one or more observational databases by extraction component 202 at 702b as described above.

If it is determined at 704b that the number of disease states are known, at 708b, computer-implemented method 700b can comprise generating (e.g., via disease status index system 102 and/or model component 108) one or more probability distributions of one or more of the disease states based on the observational data. For example, as described above with reference to FIG. 1, model component 108 can employ a probabilistic model (e.g., a hidden Markov model, a probabilistic RNN model, etc.) to generate one or more probability distributions of one or more of the disease states based on the observational data.

At 710b, computer-implemented method 700b can comprise generating (e.g., via disease status index system 102, model component 108, index component 110, etc.) a disease status index (e.g., disease status index 402) based on the one or more probability distributions. For example, as described above with reference to FIGS. 1, 2, 3, and 4, index component 110 can generate disease status index 402 (e.g., a continuous disease status index, a continuous-time disease status index, etc.) based on the one or more probability distributions that can be generated by model component 108 using a probabilistic model (e.g., a hidden Markov model, a probabilistic RNN model, etc.).

For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Figure 8:
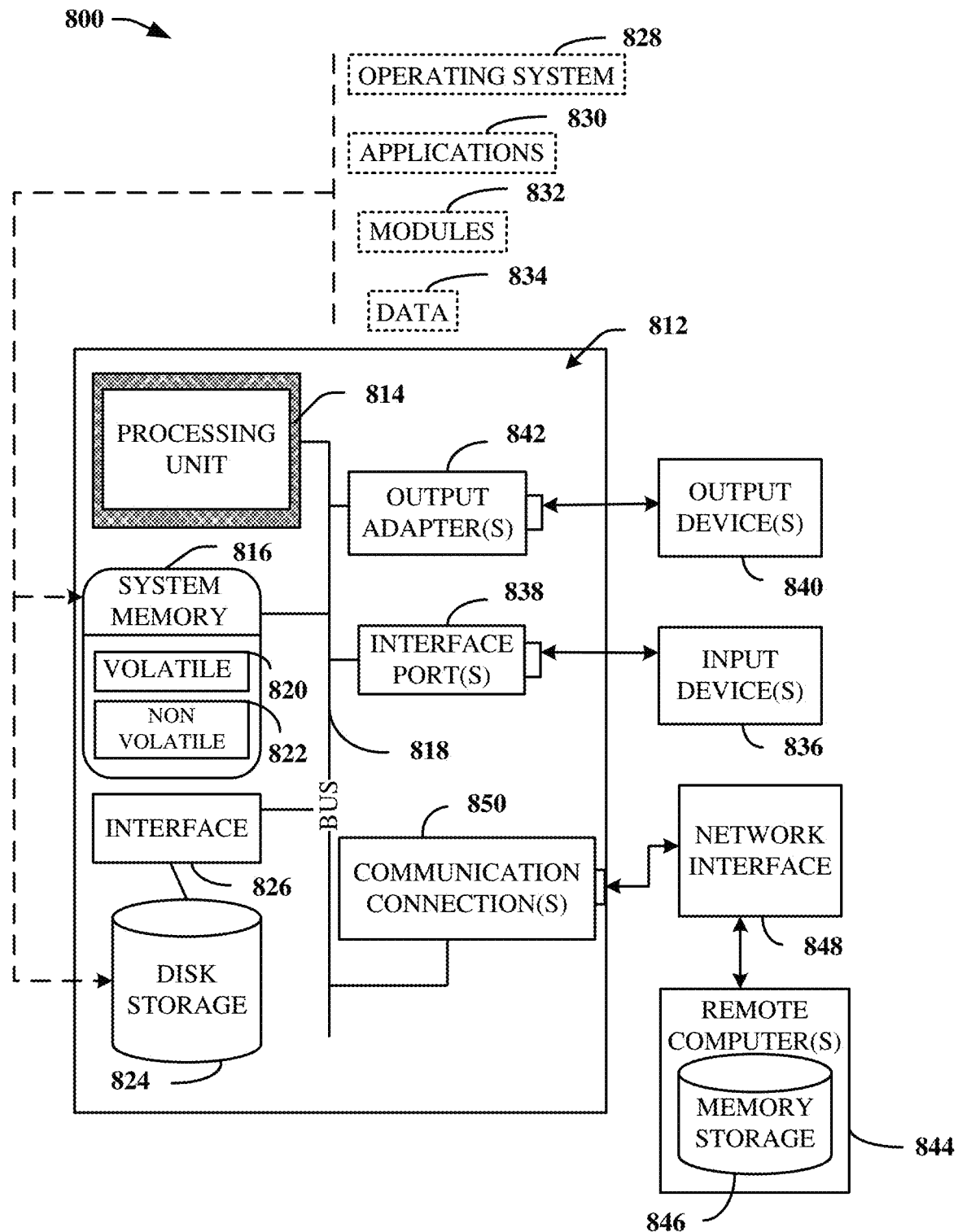
FIG. 8 illustrates a block diagram of an example, non-limiting operating environment in which one or more embodiments described herein can be facilitated.

In order to provide a context for the various aspects of the disclosed subject matter, FIG. 8 as well as the following discussion are intended to provide a general description of a suitable environment in which the various aspects of the disclosed subject matter can be implemented. FIG. 8 illustrates a block diagram of an example, non-limiting operating environment in which one or more embodiments described herein can be facilitated. Repetitive description of like elements employed in other embodiments described herein is omitted for sake of brevity.

With reference to FIG. 8, a suitable operating environment 800 for implementing various aspects of this disclosure can also include a computer 812. The computer 812 can also include a processing unit 814, a system memory 816, and a system bus 818. The system bus 818 couples system components including, but not limited to, the system memory 816 to the processing unit 814. The processing unit 814 can be any of various available processors. Dual microprocessors and other multiprocessor architectures also can be employed as the processing unit 814. The system bus 818 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 816 can also include volatile memory 820 and nonvolatile memory 822. The basic input/output system (BIOS), containing the basic routines to transfer information between elements within the computer 812, such as during start-up, is stored in nonvolatile memory 822. Computer 812 can also include removable/non-removable, volatile/non-volatile computer storage media. FIG. 8 illustrates, for example, a disk storage 824. Disk storage 824 can also include, but is not limited to, devices like a magnetic disk drive, floppy disk drive, tape drive, Jaz drive, Zip drive, LS-100 drive, flash memory card, or memory stick. The disk storage 824 also can include storage media separately or in combination with other storage media. To facilitate connection of the disk storage 824 to the system bus 818, a removable or non-removable interface is typically used, such as interface 826. FIG. 8 also depicts software that acts as an intermediary between users and the basic computer resources described in the suitable operating environment 800. Such software can also include, for example, an operating system 828. Operating system 828, which can be stored on disk storage 824, acts to control and allocate resources of the computer 812.

System applications 830 take advantage of the management of resources by operating system 828 through program modules 832 and program data 834, e.g., stored either in system memory 816 or on disk storage 824. It is to be appreciated that this disclosure can be implemented with various operating systems or combinations of operating systems. A user enters commands or information into the computer 812 through input device(s) 836. Input devices 836 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 814 through the system bus 818 via interface port(s) 838. Interface port(s) 838 include, for example, a serial port, a parallel port, a game port, and a universal serial bus (USB). Output device(s) 840 use some of the same type of ports as input device(s) 836. Thus, for example, a USB port can be used to provide input to computer 812, and to output information from computer 812 to an output device 840. Output adapter 842 is provided to illustrate that there are some output devices 840 like monitors, speakers, and printers, among other output devices 840, which require special adapters. The output adapters 842 include, by way of illustration and not limitation, video and sound cards that provide a means of connection between the output device 840 and the system bus 818. It should be noted that other devices and/or systems of devices provide both input and output capabilities such as remote computer(s) 844.

Computer 812 can operate in a networked environment using logical connections to one or more remote computers, such as remote computer(s) 844. The remote computer(s) 844 can be a computer, a server, a router, a network PC, a workstation, a microprocessor based appliance, a peer device or other common network node and the like, and typically can also include many or all of the elements described relative to computer 812. For purposes of brevity, only a memory storage device 846 is illustrated with remote computer(s) 844. Remote computer(s) 844 is logically connected to computer 812 through a network interface 848 and then physically connected via communication connection 850. Network interface 848 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 850 refers to the hardware/software employed to connect the network interface 848 to the system bus 818. While communication connection 850 is shown for illustrative clarity inside computer 812, it can also be external to computer 812. The hardware/software for connection to the network interface 848 can also include, for exemplary purposes only, internal and external technologies such as, modems including regular telephone grade modems, cable modems and DSL modems, ISDN adapters, and Ethernet cards.

Figure 9:
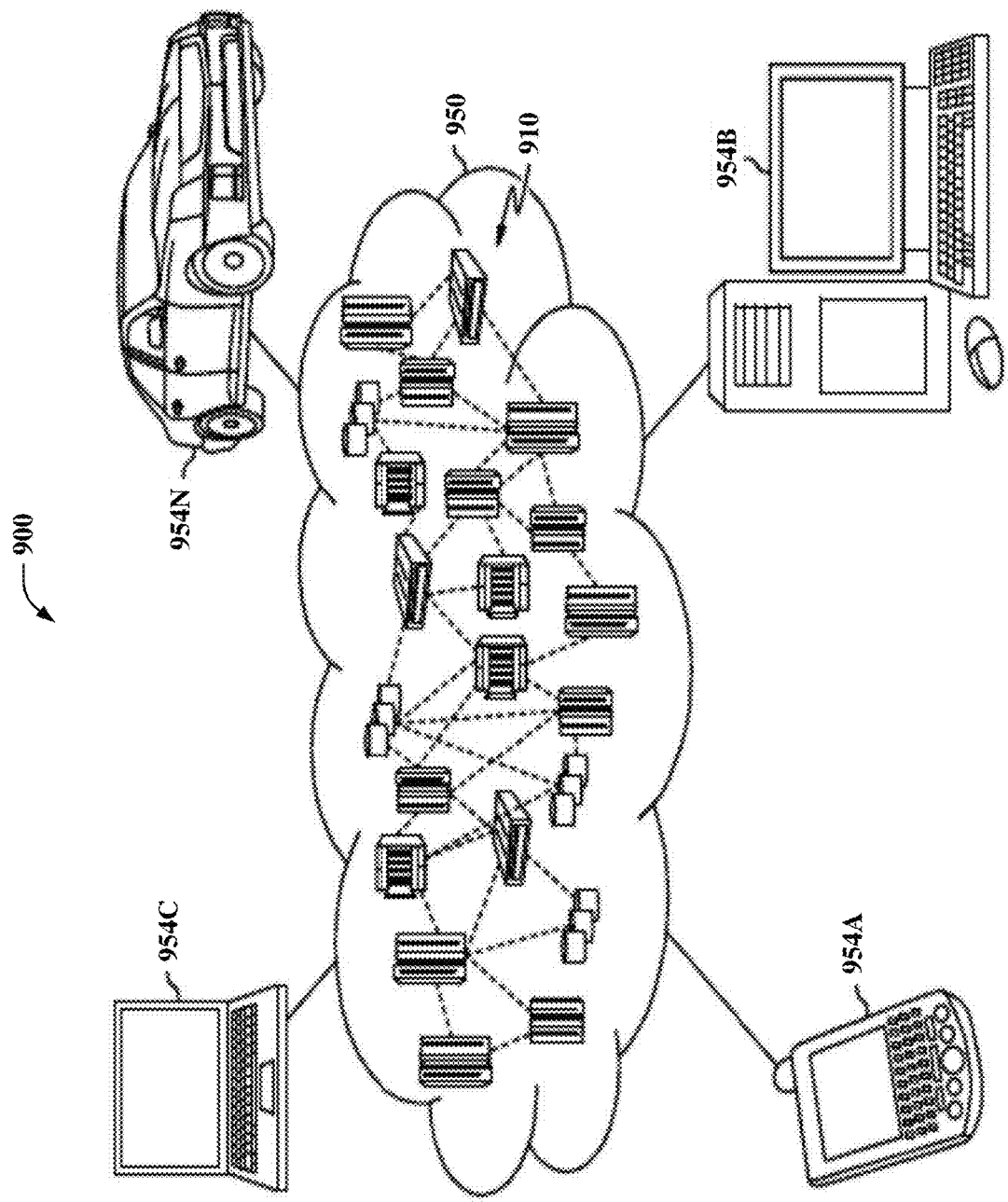
FIG. 9 illustrates a block diagram of an example, non-limiting cloud computing environment in accordance with one or more embodiments of the subject disclosure.

Referring now to FIG. 9, an illustrative cloud computing environment 950 is depicted. As shown, cloud computing environment 950 includes one or more cloud computing nodes 910 with which local computing devices used by cloud consumers, such as, for example, personal digital assistant (PDA) or cellular telephone 954A, desktop computer 954B, laptop computer 954C, and/or automobile computer system 954N may communicate via network 900. Although not illustrated in FIG. 9, cloud computing nodes 910 can further comprise a quantum platform (e.g., quantum computer, quantum hardware, quantum software, etc.) with which local computing devices used by cloud consumers can communicate. Nodes 910 may communicate with one another. They may be grouped (not shown) physically or virtually, in one or more networks, such as Private, Community, Public, or Hybrid clouds as described hereinabove, or a combination thereof. This allows cloud computing environment 950 to offer infrastructure, platforms and/or software as services for which a cloud consumer does not need to maintain resources on a local computing device. It is understood that the types of computing devices 954A-N shown in FIG. 9 are intended to be illustrative only and that computing nodes 910 and cloud computing environment 950 can communicate with any type of computerized device over any type of network and/or network addressable connection (e.g., using a web browser).

Figure 10:
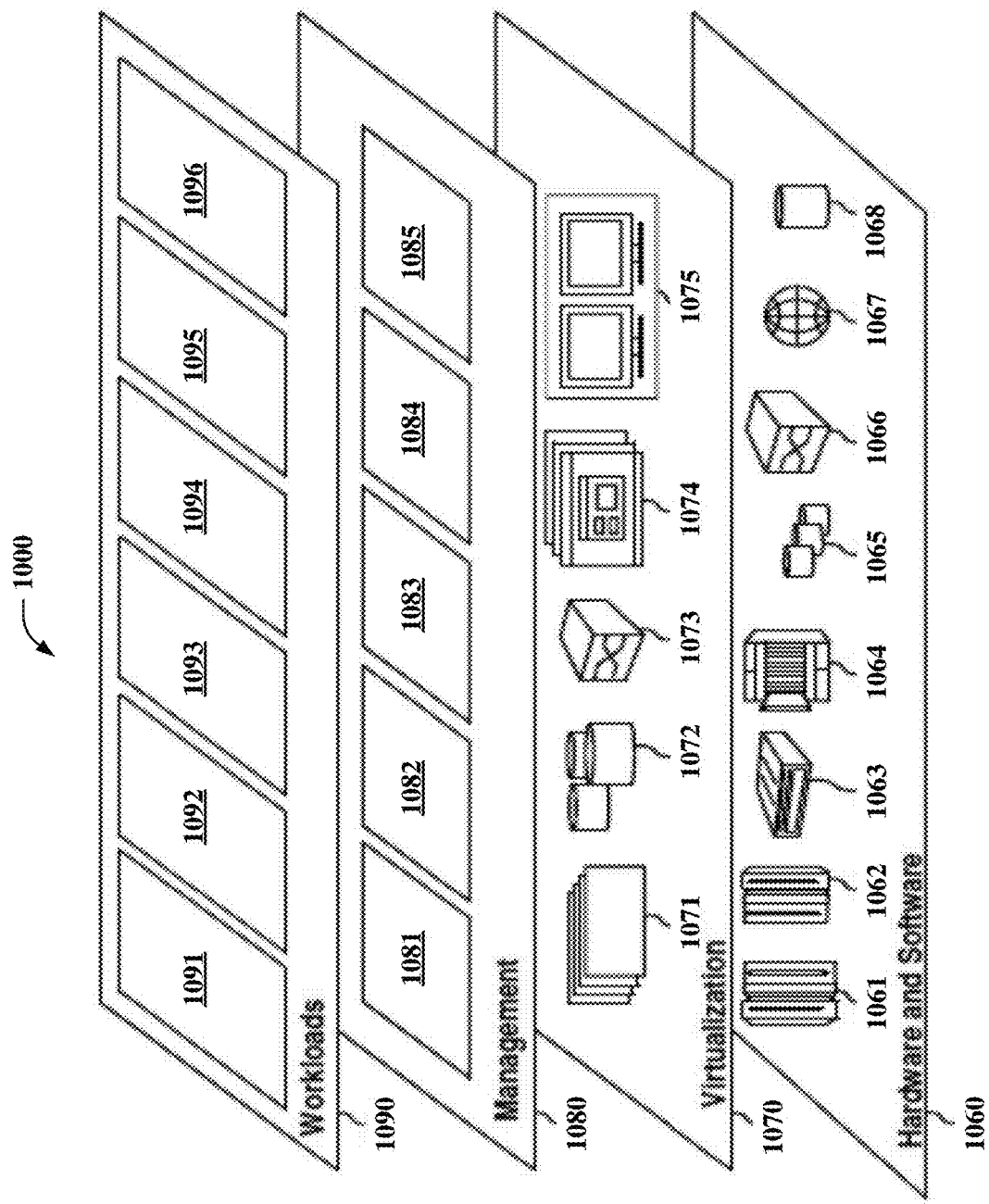
FIG. 10 illustrates a block diagram of example, non-limiting abstraction model layers in accordance with one or more embodiments of the subject disclosure.

Referring now to FIG. 10, a set of functional abstraction layers 1000 provided by cloud computing environment 950 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 1060 includes hardware and software components. Examples of hardware components include: mainframes 1061; RISC (Reduced Instruction Set Computer) architecture based servers 1062; servers 1063; blade servers 1064; storage devices 1065; and networks and networking components 1066. In some embodiments, software components include network application server software 1067, quantum platform routing software 1068, and/or quantum software (not illustrated in FIG. 10).

Virtualization layer 1070 provides an abstraction layer from which the following examples of virtual entities may be provided: virtual servers 1071; virtual storage 1072; virtual networks 1073, including virtual private networks; virtual applications and operating systems 1074; and virtual clients 1075.

In one example, management layer 1080 may provide the functions described below. Resource provisioning 1081 provides dynamic procurement of computing resources and other resources that are utilized to perform tasks within the cloud computing environment. Metering and Pricing 1082 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1083 provides access to the cloud computing environment for consumers and system administrators. Service level management 1084 provides cloud computing resource allocation and management such that required service levels are met. Service Level Agreement (SLA) planning and fulfillment 1085 provide pre-arrangement for, and procurement of, cloud computing resources for which a future requirement is anticipated in accordance with an SLA.

Workloads layer 1090 provides examples of functionality for which the cloud computing environment may be utilized. Non-limiting examples of workloads and functions which may be provided from this layer include: mapping and navigation 1091; software development and lifecycle management 1092; virtual classroom education delivery 1093; data analytics processing 1094; transaction processing 1095; and disease status index software 1096.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices. For example, in one or more embodiments, computer executable components can be executed from memory that can include or be comprised of one or more distributed memory units. As used herein, the term "memory" and "memory unit" are interchangeable. Further, one or more embodiments described herein can execute code of the computer executable components in a distributed manner, e.g., multiple processors combining or working cooperatively to execute code from one or more distributed memory units. As used herein, the term "memory" can encompass a single memory or memory unit at one location or multiple memories or memory units at one or more locations.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory that stores computer executable components; and
   a processor that executes the computer executable components stored in the memory, wherein the computer executable components comprise:
      a trainer component that:
         generates, based on first observational data comprising structured observational data and unstructured observational data of multiple entities collected at multiple observation times, structured observational training data, and
         trains a probabilistic model to generate probability distributions of disease states of diseases based on the structured observational training data, wherein the probabilistic model comprises an observational layer that groups observations of the first observational data into comorbidities of the multiple entities, and a comorbidity layer that generates respective onset patterns of the comorbidities using a set of Markov chains, and a Markov jump process layer that employs a hidden Markov model to generate the probability distributions of the disease states of the diseases by modeling transitions of the disease states of the diseases using the respective onset patterns of the comorbidities;
      a model component that employs the probabilistic model to generate probability distributions of disease states of a disease of an entity based on second observational data of the entity; and
      an index component that:
         generates, using the probabilistic model, an index value of a disease status index of the disease for the entity based on the probability distributions of the disease states of the disease of the entity, wherein the disease status index comprises:
            integer values representing the disease states, and
            non-integer values representing granular progression of the disease between the disease states;
         determines, using the probabilistic model, a dosage of the medication for the entity based on the index value of the disease status index for the entity being a non-integer value between two of the disease states; and
         controls a medication dispenser to dispense the dosage of the medication to the entity.

2. The system of claim 1, wherein at least one of the first observational data or the second observational data is selected from a group consisting of longitudinal observational data, high dimensional observational data, heterogeneous observational data, high dimensional longitudinal heterogeneous observational data, disease registry data, and electronic health record data.

3. The system of claim 1, wherein the index component further generates a patient cohort specific to a particular stage of the disease represented by the disease status index for a treatment evaluation model.

4. The system of claim 1, wherein the trainer component further trains the probabilistic model to determine at least one of a number of disease states corresponding to different diseases or one or more parameters used to generate the probability distributions corresponding to the number of disease states of the different diseases based on the structured observational training data.

5. The system of claim 1, wherein the computer executable components further comprise:
   an extraction component that extracts from an observational database at least one of the structured observational data, the unstructured observational data, or the second observational data of the entity.

6. The system of claim 1, wherein the model component employs the probabilistic model to generate the probability distributions of the disease states at multiple observation times of the entity.

7. The system of claim 1, wherein the index component generates the disease status index of the disease at multiple observation times of the entity to track at least one of status of the disease or progression of the disease, thereby facilitating at least one of improved accuracy of the disease status index or improved prognosis of the disease by an expert entity.

8. A computer-implemented method, comprising:
generating, by a system operatively coupled to a processor, based on first observational data comprising structured observational data and unstructured observational data of multiple entities collected at multiple observation times, structured observational training data, and
training, by the system, a probabilistic model to generate probability distributions of disease states of diseases based on the structured observational training data, wherein the probabilistic model comprises an observational layer that groups observations of the first observational data into comorbidities of the multiple entities, and a comorbidity layer that generates respective onset patterns of the comorbidities using a set of Markov chains, and a Markov jump process layer that employs a hidden Markov model to generate the probability distributions of the disease states of the diseases by modeling transitions of the disease states of the diseases using the respective onset patterns of the comorbidities;
generating, by the system, using the probabilistic model, probability distributions of disease states of a disease of an entity based on second observational data of the entity;
generating, by the system, using the probabilistic model, an index value of a disease status index of the disease for the entity based on the probability distributions of the disease states of the disease of the entity, wherein the disease status index comprises:
integer values representing the disease states, and
non-integer values representing granular progression of the disease between the disease states;
determining, by the system, using the probabilistic model, a dosage of the medication for the entity based on the index value of the disease status index for the entity being a non-integer value between two of the disease states; and
controlling, by the system, a medication dispenser to dispense the dosage of the medication to the entity.

9. The computer-implemented method of claim 8, wherein at least one of the first observational data or the second observational data is selected from a group consisting of longitudinal observational data, high dimensional observational data, heterogeneous observational data, high dimensional longitudinal heterogeneous observational data, disease registry data, and electronic health record data.

10. The computer-implemented method of claim 8, wherein the disease status index comprises a continuous disease status index.

11. The computer-implemented method of claim 8, further comprising:
training, by the system, the probabilistic model to determine at least one of a number of disease states corresponding to different diseases or one or more parameters used to generate the probability distributions corresponding to the number of disease states of the different diseases based on the structured observational training data.

12. The computer-implemented method of claim 8, further comprising:
extracting, by the system, from an observational database at least one of the structured observational data, the unstructured observational data, or the structured observational data of the entity.

13. The computer-implemented method of claim 8, further comprising:
employing, by the system, the probabilistic model to generate the probability distributions of the disease states at multiple observation times of the entity.

14. The computer-implemented method of claim 8, further comprising:
generating, by the system, the disease status index of the disease at multiple observation times of the entity to track at least one of status of the disease or progression of the disease, thereby facilitating at least one of improved accuracy of the disease status index or improved prognosis of the disease by an expert entity.

15. A computer program product facilitating a process to employ a probabilistic model to generate a continuous disease status index based on observational data, the computer program product comprising a computer readable storage medium having program instructions embodied therewith, the program instructions executable by a processor to cause the processor to:
generate, by the processor, based on first observational data comprising structured observational data and unstructured observational data of multiple entities collected at multiple observation times, structured observational training data, and
train, by the processor, a probabilistic model to generate probability distributions of disease states of diseases based on the structured observational training data, wherein the probabilistic model comprises an observational layer that groups observations of the first observational data into comorbidities of the multiple entities, and a comorbidity layer that generates respective onset patterns of the comorbidities using a set of Markov chains, and a Markov jump process layer that employs a hidden Markov model to generate the probability distributions of the disease states of the diseases by modeling transitions of the disease states of the diseases using the respective onset patterns of the comorbidities;
generate, by the processor, using the probabilistic model, probability distributions of disease states of a disease of an entity based on second observational data of the entity; and
generate, by the processor, using the probabilistic model, an index value of a disease status index of the disease for the entity based on the probability distributions of the disease states of the disease of the entity, wherein the disease status index comprises:
integer values representing the disease states, and
non-integer values representing granular progression of the disease between the disease states;
determine, by the processor, using the probabilistic model, a dosage of the medication for the entity based on the index value of the disease status index for the entity being a non-integer value between two of the disease states, and
control, by the processor, a medication dispenser to dispense the dosage of the medication to the entity.

16. The computer program product of claim 15, wherein at least one of the first observational data or the second observational data is selected from a group consisting of longitudinal observational data, high dimensional observational data, heterogeneous observational data, high dimensional longitudinal heterogeneous observational data, disease registry data, and electronic health record data.

17. The computer program product of claim 15, wherein the disease status index comprises a continuous disease status index.

18. The computer program product of claim 15, wherein the program instructions are further executable by the processor to cause the processor to:
- train, by the processor, the probabilistic model to determine at least one of a number of disease states corresponding to different diseases or one or more parameters used to generate the probability distributions corresponding to the number of disease states of the different diseases based on the structured observational training data.

19. The computer program product of claim 15, wherein the program instructions are further executable by the processor to cause the processor to:
- employ, by the processor, the probabilistic model to generate the probability distributions of the disease states at multiple observation times of the entity.

20. The computer program product of claim 15, wherein the program instructions are further executable by the processor to cause the processor to:
- generate, by the processor, the disease status index of the disease at multiple observation times of the entity to track at least one of status of the disease or progression of the disease.

* * * * *